| United States Patent [19] | [11] Patent Number: 4,529,600 |
| Dawson et al. | [45] Date of Patent: Jul. 16, 1985 |

[54] PENTADEUTERIORETINOIDS

[75] Inventors: Marcia I. Dawson, Los Altos; Peter D. Hobbs, Woodside, both of Calif.

[73] Assignee: SRI International, Menlo Park, Calif.

[21] Appl. No.: 416,263

[22] Filed: Sep. 9, 1982

[51] Int. Cl.$^3$ .................. A61K 31/215; C07C 69/608; C07C 103/00; C07C 103/30
[52] U.S. Cl. .................... 514/529; 260/404; 260/405.5; 260/410.5; 260/410.9 V; 514/557; 514/613; 514/859; 514/861; 514/863
[58] Field of Search ............... 424/315, 305, 320, 324, 424/318; 260/404, 405.5, 410.5, 410.9 V

[56] References Cited

U.S. PATENT DOCUMENTS

| 3,781,314 | 12/1973 | Bollag et al. | 260/410.9 |
| 4,129,662 | 12/1978 | Gander et al. | 424/305 |
| 4,190,594 | 2/1980 | Gander et al. | 260/404 |
| 4,193,931 | 3/1980 | Loeliger | 424/308 |
| 4,216,224 | 8/1980 | Yu et al. | 424/286 |

OTHER PUBLICATIONS

Verma et al., *Cancer Research*, 39, pp. 419–425, Feb. 1979.
Bouthwell et al., *Advances in Enzyme Regulation*, vol. 17, pp. 89–112, Pergamon Press Oxford and New York, 1979.
Dawson et al., I, *J. Med. Chem.*, 23, pp. 1013–1022, Sep. 1980.
Dawson et al., II, *J. Med. Chem.*, 24, pp. 583–592, May 1981.
Dawson et al., III, *J. Med. Chem.*, 24, pp. 1214–1223, Oct. 1981.

*Primary Examiner*—Natalie Trousof
*Assistant Examiner*—Vera C. Clarke
*Attorney, Agent, or Firm*—Ciotti & Murashige

[57] ABSTRACT

Retinoic acid-4,4,18,18,18-d$_5$ and esters and amides thereof are disclosed. These compounds are useful as chemopreventive agents for inhibiting tumor promotion in epithelial cells and for treating nonmalignant skin disorders.

10 Claims, No Drawings

PENTADEUTERIORETINOIDS

Reference to Government Grant or Contract

The invention described herein was made in the course of work under grant or contract from the National Institute of Health.

DESCRIPTION

1. Technical Field

The invention is in the fields of retinoid chemistry and chemotherapy. More particularly, the invention relates to deuterated analogues of retinoic acid and retinoic acid derivatives.

2. Background Art

The progressive loss of the regulation of cellular differentiation by epithelial cells can result in cancer. Retinoic acid and some of its analogues (retinoids) have been investigated as "chemopreventive" agents that is, agents that interfere with tumor promotion in epithelial cells. Boutwell, R. K.; et al, *Advances in Enzyme Regulation* V.17, Ed. Weber, G., Pergamon Press (1979); Verma, A. K.; et al, *Cancer Res* (1979) 39:419–427; Dawson, M. I.; et al, *J Med Chem* (1980) 23:1013–1022 and *J Med Chem* (1981) 24:583–592.

Various other retinoids have been reported as having antitumor activity or other biological activity such as activity against skin disorders. U.S. Pat. Nos. 3,781,341, 4,129,662, 4,190,594, 4,193,931, and 4,216,224.

An object of the present invention is to provide novel retinoids that are active chemopreventive and therapeutic agents but whose metabolic deactivation is reduced due to deuteration of particular sites of the retinoid structure. Such deactivation allows these novel deuterated retinoids to have a longer duration of action so that they can be administered at reduced dosages.

DISCLOSURE OF THE INVENTION

The compounds of the invention are deuterated retinoids of the following formula:

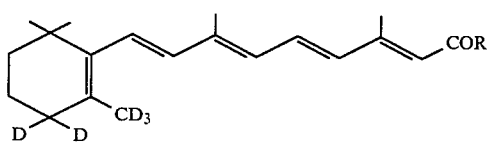

where R is hydroxyl, alkoxy of 1 to about 8 carbon atoms, or $NR^1R^2$ where $R^1$ is hydrogen, alkyl, or aryl and $R^2$ is alkyl or aryl, and 13-cis isomers thereof.

When used as pharmaceutical agents one or more of these pentadeuterioretinoids is combined with a suitable pharmaceutically acceptable carrier and an effective dose thereof is administered to the patient.

MODES FOR CARRYING OUT THE INVENTION

The alkyl group of the esters of pentadeuterioretinoic acid represented by formula (1) may be straight chain or branched chain. They preferably contain 1 to 4 carbon atoms. Examples of such alkyl groups are methyl, ethyl, propyl, isopropyl, n-butyl, 2-methylpropyl, n-amyl, n-hexyl, 2-methylamyl, n-heptyl, 2-ethylhexyl and n-octyl. Examples of the esters represented by formula (1) are the E and 13Z isomers of methyl retinoate-4,4,18,18,18-$d_5$ ethyl retinoate-4,4,18,18,18-$d_5$, propyl retinoate-4,4,18,18,18-$d_5$, butyl retinoate-4,4,18,18,18-$d_5$, isobutyl retinoate-4,4,18,18,18-$d_5$, hexyl retinoate-4,4,18,18,18-$d_5$, and octyl retinoate-4,4,18,18,18-$d_5$.

The alkyl groups ($R^1$ and $R^2$) of the amides represented by formula (1) may also be straight chain or branched chain. They will typically each contain 1 to 8 carbon atoms, preferably 1 to 4 carbon atoms and have 0 or 1 hydroxy substituent. Examples of such alkyl groups are those mentioned above and hydroxy methyl, 2-hydroxyethyl, 3-hydroxypropyl, 2-hydroxyhexyl, and the like. The corresponding aryl groups represented by $R^1$ and/or $R^2$ may be substituted or unsubstituted mononuclear or polynuclear moities. The substituents will usually be lower (i.e., 1 to 4 carbon atoms) alkyl, lower alkoxy, or hydroxy. Examples of such groups are phenyl, o-, m-, or p-hydroxyphenyl, o-, m-, or p-methoxyphenyl, ethylbenzyl, cumyl, naphthyl, phenanthryl, azulyl, and the like. These aryl groups will typically contain 6 to about 15 carbon atoms. Phenyl, 4-hydroxyphenyl, and 4-methoxyphenyl are preferred aryl groups. Examples of amides represented by formula (1) are the E and 13Z isomers of N-methyl retinamide-4,4,18,18,18-$d_5$, N-(2-hydroxyethyl) retinamide-4,4,18,18,18-$d_5$, N-isopropyl retinamide-4,4,18,18,18-$d_5$, N-butyl retinamide-4,4,18,18,18-$d_5$, N-hexyl retinamide-4,4,18,18,18-$d_5$, N-octyl retinamide-4,4,18,18,18-$d_5$, N,N-dimethyl retinamide-4,4,18,18,18-$d_5$, N-ethyl-N-methyl retinamide-4,4,18,18,18-$d_5$, N-isopropyl-N-methyl retinamide-4,4,18,18,18-$d_5$, N,N-diethyl retinamide-4,4,18,18,18-$d_5$, N-butyl-N-ethyl retinamide-4,4,18,18,18-$d_5$, N-methyl-N-octyl retinamide-4,4,18,18,18-$d_5$, N-phenyl retinamide-4,4,18,18,18-$d_5$, N-(4-hydroxyphenyl) retinamide-4,4,18,18,18-$d_5$, N-(4-methoxyphenyl) retinamide-4,4,18,18,18-$d_5$, N-naphthyl retinamide-4,4,18,18,18-$d_5$, N-methyl-N-phenyl retinamide-4,4,18,18,18-$d_5$, and N-tolyl retinamide-4,4,18,18,18-$d_5$.

The reaction sequence for making the pentadeuterioretinoic acid esters of formula (1) is given below.

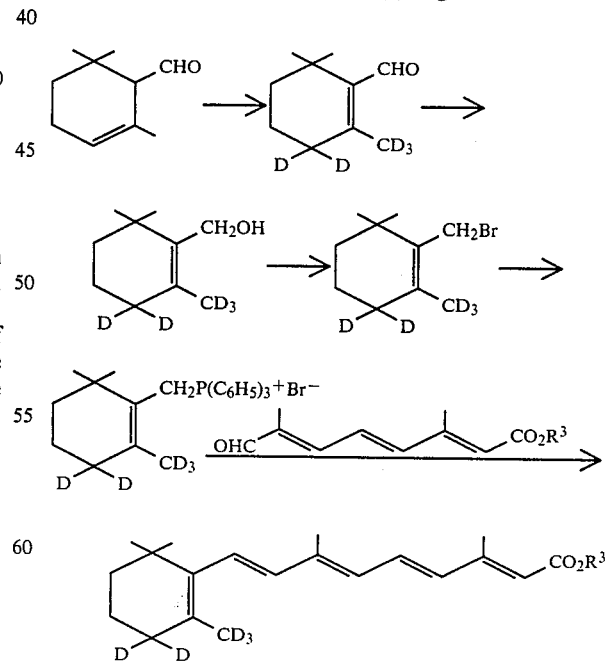

where $R^3$ is the alkyl group of the above mentioned alkoxy group. In the initial step of the sequence α-cyclocitral is equilibrated to the β isomer with sodium methoxide in methyl alcohol-d or the β isomer is treated in the same manner and the base is quenched with acetic acid-d$_4$ or acetic acid-d to give deuterated β-cyclocitral. The deuterated β-cyclocitral is then reduced to yield deuterated β-cyclogeraniol. The phosphonium salt is prepared from the alcohol and converted to the ylide. The ylide is then reacted with the trienal ester to produce the deuterated retinoate. The corresponding acid is obtained by alkaline hydrolysis of the ester. Amides may be prepared from the deuterated acid by conversion to the chloride and reaction of the deuterated retinoyl chloride with a suitable alkyl or aryl amine or by reaction of the acid with a suitable activating agent, such as N,N-carbonyldimidazole, and an amine.

The following examples further illustrate the invention compounds and their synthesis. These examples are not intended to limit the invention in any manner. The subscript R indicates use of the retinoid numbering system.

EXAMPLE 1

Ethyl (E)-Retinoate-4,4,18,18,18-d$_5$

A solution of 1 M sodium methoxide was prepared from 0.81 g (0.035 g-at) of Na in 35 mL of methanol-d (Aldrich, 99.5 atom % d). Purified α-cyclocitral (5.32 g, 35 mmol) in 3 mL of methanol-d was introduced under argon. The orange solution was allowed to stand for 70 hr, acidified with 3.5 g (55 mmol) of acetic acid-d$_4$ (Aldrich, 99.5 atom % d), and diluted with 200 mL of water. The deuterated crude β-cyclocitral was extracted into 100 mL of hexane, washed twice with 30 mL of brine, and dried (Na$_2$SO$_4$), and the solvent was evaporated. The product was immediately dissolved in 3 mL of methanol-d and added to 35 mL of a fresh solution of sodium methoxide in methanol-d prepared as before. The second equilibration was allowed to proceed for 91 hr, then quenched with 3 g (47 mmol) acetic acid-d$_4$, and the aldehyde was isolated. A third equilibration was performed similarly. The base was neutralized after 69 hr, and 4.7 g of deuterated β-cyclocitral was obtained as an orange oil.

The total crude reaction product (4.7 g, 30 mmol) in 15 mL of tetrahydrofuran (THF) was treated at room temperature under argon with 72 mL of 0.5 M 9-borabicyclo[3.3.1]nonane (36 mmol) in THF. The reaction mixture was allowed to stand at room temperature for 24 hr. The solvent was evaporated, the viscous residue was dissolved in 400 mL of ether, and 2.2 g (36 mmol) of 2-aminoethanol was added with stirring. After 80 min at room temperature and 1.5 hr at −5° C., the precipitate was filtered and washed with 100 mL of ether, and the filtrate was evaporated. The residue was chromatographed on a 4.5×40-cm silica gel column. Elution with 1.5-L volumes of 5, 6, 7, and 8% ethyl acetate/hexane (100 to 200-mL fractions) afforded a liquid mixture of α- and β-cyclogeraniols, followed by 3.90 g (70%) of crystalline β-cyclogeraniol-d$_5$: IR (film) 3350 (OH), 2260, 2210, 2180, 2130, 2080 (CD), 1655, 1420, 1335, 1305, 1250, 1170, 1120, 1015, 995 cm$^1$; $^1$H NMR (CDCl$_3$) δ 1.06 [s, 6, (CH$_3$)$_2$C], 1.25–2.09 (m, 4, C$_R$-2,3 CH$_2$, 1, OH), 4.15 (s, 2, CH$_2$O); MS, m/e 157 (d$_3$), 0.4%; 158 (d$_4$), 6.4%; 159 (d$_5$), 87.4%, 160 (d$_6$), 5.8%, MS calcd for C$_{10}$H$_{13}$D$_5$O, 159.1671; found, 159.1670.

The deuterated β-cyclogeraniol (3.18 g, 20 mmol) dissolved in 6 mL of hexane and 25 mL of ethyl ether containing 0.5 mL of pyridine was treated with a solution of 1.0 mL (10 mmol) of PBr$_3$ in 5 mL of hexane over a 65-min period at −10° to −15° C. The mixture was cooled for 1 hr and then allowed to warm to room temperature over 1.5 hr. The product was extracted into 50-mL of hexane from 125 mL of ice-brine, washed with 50-mL volumes of brine, saturated NaHCO$_3$, and brine (twice). The solution was dried (Na$_2$SO$_4$) and concentrated at reduced pressure. The crude bromide was dissolved in 10 mL of CH$_2$Cl$_2$ containing 7.1 g (26 mmol) of (C$_6$H$_5$)$_3$P and allowed to stand at room temperature for 40 hr. The residue remaining after concentration was triturated with 80 mL of ethyl acetate to separate out an oil, which rapidly crystallized. After 7 hr at room temperature and 70 hr at −5° C., the solid was filtered, dried at 120° C. (0.2 mm) for 4.5 hr, washed successively with 100-mL portions of ethyl acetate and hexane, and again dried at 120°–130° C. (0.2–0.4 mm) for 6 hr. The white salt, 6,6-dimethyl-2-methyl-d$_3$-1-cyclohexen-3,3-d$_2$-1-yl-methyltriphenylphosphonium bromide—mp 206°–207.5° C.—weighed 8.10 g (84%); IR (mull) 2150, 2070 (CD), 1590, 1430, 1400, 1340, 1315, 1250, 1155, 1105, 1080, 1000, 890, 855, 815, 735, 720, 690 cm$^{-1}$; $^1$H NMR (CDCl$_3$) δ 0.81 [s, 6, (CH$_3$)$_2$C], 1.3–1.7 (m, 4, C$_R$-2,3 CH$_2$, 0.35, remaining allylic CH$_2$ and CH$_3$), 4.37 (d, J=14 Hz, 2, CH$_2$P), 7.6–8.0 [m, 15, (C$_6$H$_5$)$_3$P].

To a suspension of 7.9 g. (16.3 mmol) of the deuterated β-cyclogeranylphosphonium salt in 15 mL of THF at −30° C. under argon, was added 13.5 mL of 1.19 M n-butyllithium (16 mmol) in hexane. The deep red suspension was allowed to warm to 0° C. over a 1-hr period before a solution of 3.75 g (18 mmol) of freshly recrystallized (cyclohexane) (E)-7-carboethoxy-2,6-dimethylhepta-2,4,6-trienal in 6 mL of THF was introduced. The reaction was stirred at room temperature for 17 hr and then heated at 60° C. for 1 hr. The dark suspension was next cooled, poured into 120 mL of water containing 1 mL of acetic acid and 0.1 g of TBHQ, and extracted with 100 mL of 10% ethyl acetate/hexane. The extract was washed twice with brine, dried (Na$_2$SO$_4$), and concentrated under nitrogen. The residue was chromatographed on a 4×40-cm silica gel column (1.5% ethyl acetate/hexane). The 4.17 g of crude ester, a yellow gum, contained a minor, less-polar impurity as shown by silica gel TLC (10% ethyl acetate/hexane) and, therefore, was repurified by HPLC on two Waters Prep Pak-500 silica gel cartridges in series (1% ethyl acetate/hexane). The product, ethyl (E)-retinoate-4,4,18,18,18-d$_5$, weighed 3.53 g (66%) and had IR and $^1$H NMR spectra identical to those of a previously prepared sample; $^{13}$C NMR (CDCl$_3$) 167.2 (C$_R$-15), 152.7 (C$_R$-13), 139.5 (C$_R$-9), 137.9 (C$_R$-6), 137.3 (C$_R$-8), 135.3 (C$_R$-12), 130.9 (C$_R$-11), 129.6 (C$_R$-5,10), 128.7 (C$_R$-7), 118.7 (C$_R$-14), 59.6 (OCH$_2$), 39.7 (C$_R$-2), 34.3 (C$_R$-1), 29.0 (C$_R$-16,17), 19.1 (C$_R$-3), 14.4 (CH$_2$CH$_3$), 13.9 (C$_R$-20), 12.9 ppm (C$_R$-19); UV EtOH λ$_{max}$ 355 nm ($\epsilon$ 4.52×10$^4$); MS m/e 331 (d$_3$), 0.6%; 332 (d$_4$), 7.1%; 333 (d$_5$), 90.5%; 334 (d$_6$), 1.1%; 335 (d$_7$), 0.5%; MS calcd for C$_{22}$H$_{27}$D$_5$O$_2$ 333.2716, found 333.2696.

EXAMPLE 2

(E)-Retinoic Acid-4,4,18,18-d$_5$

A solution of 1.48 g (4.4 mmol) of the deuterated ethyl retinoate of Example 1 in 4 mL of ethanol was added under argon to a degassed (4 times) solution of 0.7 g (12 mmol) KOH in 2.5 mL of water and 4 mL of ethanol. The suspension was heated to 80° C. for a 20-min period, and the temperature was maintained there for 12 min. The oil dissolved at 80° C. The cooled yellow solution was acidified with 10 mL of 50% acetic acid and diluted with 50 mL of water. The precipitated acid was extracted into ethyl ether (2×30 mL). The ethereal solution was washed with brine (2×15 mL) and dried ($Na_2SO_4$). The crude acid remaining after concentration was extracted under nitrogen with 20 mL of hot methanol. The first crop of bright yellow crystals, mp 175.5°–177.5° C., was obtained on cooling and weighed 0.75 g (56%): HPLC ($\mu$ Bondapak $C_{18}$, 80% $MeCN/H_2O$, 2.0 mL/min, 280 nm) $t_R$ 1.3 (0.4%), 4.4 min (99.6%); IR (mull) 3300–2300 (OH), 1685 (C=O), 1600, 1570, 1415, 1345, 1265, 1250, 1185, 1165, 970, 950, 925 $cm^{-1}$; $^1H$ NMR ($CDCl_3/DMSO-d_6$) $\delta$ 1.03 (s, 6, $C_R$-16,17 $CH_3$), 1.4–1.7 (m, 4, $C_R$-2,3, $CH_2$), 2.00 (s, 3, $C_R$-19 $CH_3$), 2.34 (d, J=Hz, 3, $C_R$-20 $CH_3$), 5.77 (s, 1, $C_R$-14 C=CH), 6.0–6.4 (m, 4, $C_R$-7, 8,12 HC=CH, C-10 C=CH); 6.98 (dd, J=15 Hz, J=11.5 Hz, 1, $C_R$-11 HC=CH); $^{13}C$ NMR ($CDCl_3/DMSO-d_6$), 168.5 ($C_R$-15), 151.8 ($C_R$-13), 138.9 ($C_R$-9), 137.7 ($C_R$-6), 136.9 ($C_R$-8), 135.2 ($C_R$-12), 130.3 ($C_R$-11), 129.2 ($C_R$-5,10), 128.3 ($C_R$-7), 119.0 ($C_R$-14), 39.6 ($C_R$-2), 34.0 ($C_R$-1), 28.8 ($C_R$-16,17), 18.8 ($C_R$-3), 13.6 ($C_R$-20), 12.6 ppm ($C_R$-19); UV (EtOH) $\lambda_{max}$ 344 nm ($\epsilon$ 4.45×$10^4$); MS m/e 303 ($d_3$), 0.8% 304 ($d_4$), 7.0%; 305 ($d_5$), 90.5%; 306 ($d_6$), 1.7%; MS calcd for $C_{20}H_{22}D_5O_2$ 305.2403, found 305.2386.

The E configuration of the deuterated acid was established by comparison of the 100-MHz $^1H$ NMR spectrum with that of an authentic sample of (E)-retinoic acid and with the published spectra of other isomers. The $^{13}C$ NMR spectrum was compared with the published spectra of retinoic acid isomers and was also in agreement with the recorded spectrum of the E isomer, except for the absence of the signals for $C_R$-4 at 33.3 ppm and $C_R$-18 at 21.6 ppm.

The pentadeuterioretinoids of formula (1) may be used topically or systemically as chemopreventive agents and in the treatment, amelioration, or prevention of the skin disorders for which retinoic acid is useful. In this regard, they may be used for therapy in animals, including humans, of premalignant epithelial cell lesions, as a prophylaxis against tumor promotion in epithelial cells and treatment for dermatoses such as icthyoses, follicular disorders, benign epithelial disorders, and other proliferative skin diseases (nonmalignant conditions of the skin that are characterized by epidermal cell proliferation or incomplete cell differentiation) such as acne, psoriasis, eczema, atopic dermatitis, nonspecific dermatitis and the like. When used for such treatments they will usually be formulated with a pharmaceutically acceptable liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles in the pharmaceutical formulation art. The carrier may be organic or inorganic in nature. Examples of pharmaceutically acceptable carriers that may be used to formulate the retinoids are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutically carriers. In addition to the retinoid and carrier the formulation may contain minor amounts of additives such as flavoring agents, coloring agents, thickening or gelling agents, emulsifiers, wetting agents, buffers, stabilizers, and preservatives such as antioxidants.

For topical administration the retinoids are conveniently provided in the form of ointments, tinctures, creams, solutions, lotions, sprays, suspensions, and the like. The amount of retinoid in such topical formulations will normally be in the range of about 0.01 to about 1% by weight. For enteral (oral or rectal) administration the retinoids will typically be formulated as tablets, capsules, dragees, syrups, solutions, or suppositories. For parenteral administration the retinoids will be formulated as injectable solutions or suspensions.

The dosages and dosage regimen in which the retinoids are administered will vary according to, the dosage form, mode of administration, the condition being treated and particulars of the patient being treated. They will, of course, be administered in chemopreventive (tumor promotion inhibiting) amounts or therapeutically effective amounts. For adult humans such chemopreventive amounts will usually be about 0.01 mg to 10.0 mg daily given in one or more doses. Oral doses will generally be less than topical doses and doses for treating skin disorders will typically be less than doses administered for chemoprevention. The dose for treating skin disorders will be on the order of, but normally less than, the dose of retinoic acid prescribed for the disorder.

The pentadeuterioretinoids of this invention may be administered at lower dose levels relative to their non-deuterated analogues because they are not as susceptible to metabolic deactivation as their nondeuterated counterparts. In this regard, a major pathway for metabolic deactivation of retinoids is allylic oxidation at the $4_R$ position of the $\beta$-cyclogeranylidene ring of the retinoid skeleton. Interference with this hydrogen-abstraction process by replacing $4_R$ hydrogen atoms with deuterium atoms reduces toxicity and increases effectiveness at comparable dose levels.

The usefulness of the invention compounds was demonstrated by testing the compound of Example 2 in the ornithine decarboxylase (ODC) assay, Verma, A. K. and Boutwell, R. K.; Cancer Res (1977) 37:2196–2201, and the tracheal organ culture assay, Newton, D. L.; Henderson, W. R.; and Sporn, M. B.; Cancer Res (1980) 40:3413–3425. The ODC assay measures a compound's effect on the prevention of the induction of ODC. The tracheal organ culture assay measures a compound's ability to reverse keratinization. For comparison purposes retinoic acid was also tested by these assays.

The ODC assay is carried out as follows. Female Charles River CD-1 mice from Charles River Breeding Laboratories, Wilmington, Mass., are used (age 7 to 9 weeks). The dorsal hair of the mice is shaved 1 to 2 days before testing, and only mice showing no hair regrowth are used. A single dose of 12-O-tetradecanoylphorbol-13-acetate (TPA) (10.5 $\mu$g, 17 nmol) in 0.2 mL of acetone is applied topically to the back of each mouse. The test compound, at one of three dose levels (1.7, 17, and 170 nmol), dissolved in 0.2 mL of acetone is applied 1 hour before the TPA treatment to the test groups; the control group is treated with acetone alone. The mice are killed by cervical dislocation five hours after TPA treatment. Determinations are done in triplicate.

The epidermis is obtained from the sacrificed animals. To obtain sufficient material, the dorsal skins from 2 to b 3 mice in each treatment group are pooled. The depilatory agent Nudit ® (Helena Rubinstein, New York) is applied to the shaved area of the skin; after 5 minutes, it is washed off thoroughly with cold tap water. Then the skin is excised and plunged immediately into ice-cold water; it is then placed in a 55° C. water bath for 30 seconds and reimmersed in ice-cold water for at least another 30 seconds. The skin is placed epidermis side up on a cold plate, and the epidermis is scraped off with a razor blade. The pooled epidermal sheets are homogenized (Polytron PT-10 homogenizer) at 0° to 4° C. for 15-20 seconds in 50 mM sodium phosphate buffer (pH 7.2) containing 0.1 mM pyridoxal phosphate and 0.1 mM ethylenediaminetetraacetic acid (EDTA), at a volume of 1 mL/skin.

The supernatant fraction remaining after centrifugation of the homogenate at 10,000×g for 30 seconds at 0° C. is used for the enzyme assay. Enzyme activity is determined using the microassay for ODC as described by Verma and Boutwell to measure the release of $^{14}CO_2$ from DL-[1-$^{14}$C]-ornithine (58 mCi/mmol) after incubation with the 10,000×g supernatant. The incubations are carried out by decanting, with a Pasteur pipette, 100 µL of the supernatant containing 100 to 120 µg of protein into two or three 15-mL Corex tubes in a shaking water bath at 37° C. The assay mixture in the tubes consists of 50 µL of 100 mM sodium phosphate buffer (pH 7.2), 10 µL of 4 mM pyridoxal phosphate, 40 µL of 25 mM dithiothreitol, and 1 µL of 0.1 M EDTA. The center wells in the tubes are filled with 200 µL of a 2:1 solution (v/v) of ethanolamine:2-methoxyethanol. The reaction is started by adding 50 µL of substrate (0.5 µCi of DL-[1-$^{14}$C]-ornithine in 2 mM cold ornithine) at 1-minute intervals by injection to each of the stoppered tubes. Incubations are routinely carried out at 37° C. for 30 to 60 minutes. The reaction is stopped by addition of 0.5 ml of 2 M citric acid, and incubation is continued for an additional hour without heating to ensure complete absorption of $^{14}CO_2$.

Radioactivity is measured using a toluene-based scintillant (4 g of PPO and 50 mg of POPOP/L of toluene) in a Beckman LS-250 liquid scintillation counter. Enzyme activity is determined in triplicate and expressed as nanomoles of $CO_2$ released in 30 minutes per milligram of protein. Enzyme activity is linear for the protein concentration used. The protein concentrations of the epidermal extracts are determined by the Lowry procedure, using bovine serum albumin as the standard.

The tracheal organ culture assay is carried out as follows. Tracheas are taken from hamsters that are in very early stages of vitamin A deficiency and placed in organ culture. At the time of culture, the animals are still gaining weight; the tracheal epithelium is generally low columnar or cuboidal, with only occasional patches of squamous metaplasia. Each trachea is opened from the larynx to the carina along the membranous dorsal wall and cultured in a serum-free medium (CMRL-1066; with crystalline bovine insulin, 0.1 µg/ml; hydrocortisone hemisuccinate, 0.1 µg/ml; glutamine, 2 mM; penicillin, 100 units/ml; and streptomycin, 100 µg/ml, added). Cultures are gassed with 50% oxygen, 45% nitrogen, and 5% $CO_2$. The culture dishes are rocked at 35.5-36.0 degrees to allow the tracheas contact with both gas and medium. All tracheas are grown in medium containing no retinoid for the first 3 days. At the end of 3 days, some tracheas are harvested; almost all of these tracheas have significant squamous metaplasia, and approximately 60% have keratinized lesions. The remaining tracheas are then divided into different groups which are treated with either: (1) retinoid dissolved in dimethylsulfoxide (final concentration of DMSO in culture medium is never greater than 0.1%) or (2) an equivalent amount of DMSO alone. Culture medium is changed three times a week, and all of the remaining tracheas are harvested at the end of 10 days in culture. Tracheas are fixed in 10% buffered formalin and embedded in paraffin. Cross sections of five micrometers are made through the mid-portion, stained with hematoxylin and eosin, and then scored with a microscope for the presence of keratin and keratohyaline granules, both of which are found in approximately 90% of control cultures that received no retinoid for the entire 10 day culture period. Retinoids are scored as "inactive" if both keratin and keratohyaline granules are seen; they are scored as "active" if neither keratin nor keratohyaline granules are seen, or if keratohyaline granules alone are absent.

The table below gives the results of these tests.

| | Reversal of Keratinization in Hamster Tracheal Organ Culture | | Inhibition of Induction of Ornithine Decarboxylase by 12-O—Tetradecanoyl-phorbol-13-acetate in Mouse Skin | |
|---|---|---|---|---|
| | Conc (M) | Active/Total Cultures (%) | Dose (nmol) | % Inhibition of Control |
| (E)-retinoic acid-4,4,18,18,18-d$_5$ | $10^{-9}$ | 8/8 (100) | 17 | 90 |
| | $10^{-10}$ | 6/7 (86) | 1.7 | 90 |
| (E)-retinoic acid | $10^{-8}$ | 236/236 (100) | | |
| | $10^{-9}$ | 419/474 (88) | 1.7 | 87-91 |
| | $10^{-10}$ | 134/256 (52) | | |

These results indicate that the deuterated retinoids of the invention possess biological activity that makes them useful as chemopreventive agents and therapeutic agents for treating nonmalignant skin disorders.

Modifications of the above described modes for carrying out the invention that are obvious to those of skill in the fields of organic chemistry, pharmaceuticals, and/or medicine are intended to be within the scope of the following claims.

We claim:

1. A compound of the formula

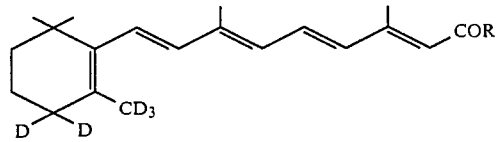

where R is hydroxyl, alkoxy of 1 to about 8 carbon atoms, or NR$^1$R$^2$ where R$^1$ is hydrogen, alkyl, or aryl and R$^2$ is alkyl or aryl and 13-cis isomers thereof.

2. The compound of claim 1 wherein said alkoxy contains 1 to 4 carbon atoms and said alkyl groups represented by R$^1$ and R$^2$ each contain 1 to 4 carbon atoms and have 0 to 1 hydroxy substituent and said aryl groups represented by R$^1$ and R$^2$ each contain 6 to about 15 carbon atoms.

3. (E)-Retinoic acid-4,4,18,18,18-d$_5$.

4. Ethyl (E)-retinoate-4,4,18,18,18-d$_5$.

5. A therapeutic composition for treating a dermatosis or a proliferative skin disease comprising a therapeutically effective amount of the compound of claim 1, 2, 3, or 4 combined with a pharmaceutically acceptable carrier.

6. A method of inhibiting tumor promotion in epithelial cells of a living animal comprising administering a tumor promotion inhibiting amount of the compound of claim 1, 2, 3, or 4 to the animal.

7. The method of claim 6 wherein the animal is a human.

8. A method of treating a living animal for a dermatosis or a proliferative skin disease comprising administering a therapeutically effective amount of the compound of claim 1, 2, 3, or 4 to the animal.

9. The method of claim 8 wherein the compound is administered topically to the affected area of skin.

10. The method of claim 8 wherein the animal is a human.

* * * * *